United States Patent
Sasai (10) Patent No.: US 12,194,317 B2
(45) Date of Patent: Jan. 14, 2025

(54) CHARGED PARTICLE BEAM IRRADIATION APPARATUS

(71) Applicant: SUMITOMO HEAVY INDUSTRIES, LTD., Tokyo (JP)

(72) Inventor: Kenzo Sasai, Tokyo (JP)

(73) Assignee: Sumitomo Heavy Industries, Ltd., Tokyo (JP)

( * ) Notice: Subject to any disclaimer, the term of this patent is extended or adjusted under 35 U.S.C. 154(b) by 171 days.

(21) Appl. No.: 17/217,546

(22) Filed: Mar. 30, 2021

(65) Prior Publication Data

US 2021/0299480 A1   Sep. 30, 2021

(30) Foreign Application Priority Data

Mar. 30, 2020   (JP) ................................ 2020-060893

(51) Int. Cl.
| | |
|---|---|
| *A61N 5/10* | (2006.01) |
| *G21K 1/02* | (2006.01) |
| *G21K 5/04* | (2006.01) |

(52) U.S. Cl.
CPC .......... *A61N 5/1081* (2013.01); *A61N 5/103* (2013.01); *A61N 5/1048* (2013.01); *G21K 1/02* (2013.01); *G21K 5/04* (2013.01); *A61N 2005/1087* (2013.01)

(58) Field of Classification Search
CPC .. A61N 2005/1087; A61N 5/10; A61N 5/177; A61N 5/1081; H05H 7/10
See application file for complete search history.

(56) References Cited

U.S. PATENT DOCUMENTS

| | | | | |
|---|---|---|---|---|
| 6,034,377 A | * | 3/2000 | Pu ........................... | G21K 5/10 |
| | | | | 250/398 |
| 9,289,624 B2 | | 3/2016 | Jongen | |
| 10,052,498 B2 | | 8/2018 | Jongen | |
| 10,799,714 B2 | | 10/2020 | Jongen | |
| 2013/0289330 A1 | * | 10/2013 | Haruna ............... | A61N 5/1081 |
| | | | | 600/1 |
| 2014/0243576 A1 | * | 8/2014 | Kakutani ............. | A61N 5/1077 |
| | | | | 250/503.1 |
| 2016/0279446 A1 | * | 9/2016 | Tachibana ............ | A61N 5/1043 |
| 2017/0013703 A1 | * | 1/2017 | Sugahara ............... | H05H 13/04 |
| 2019/0030373 A1 | * | 1/2019 | Miyashita ........... | A61N 5/1081 |

FOREIGN PATENT DOCUMENTS

JP   2015-163229 A   9/2015

* cited by examiner

*Primary Examiner* — Eliza W Osenbaugh-Stewart
(74) *Attorney, Agent, or Firm* — Michael Best & Friedrich LLP (57) ABSTRACT

There is provided a charged particle beam irradiation apparatus that performs irradiation of a charged particle beam, the apparatus including: an accelerator that accelerates a charged particle to generate the charged particle beam; an irradiator that includes a gantry rotatable around a rotation axis, and performs irradiation of the charged particle beam generated by the accelerator; and a transporter that includes an energy degrader provided outside the irradiator to reduce an energy of the charged particle beam generated by the accelerator, and transports the charged particle beam, which is generated by the accelerator, to the irradiator. The transporter transports the charged particle beam to the irradiator while maintaining an energy distribution of the charged particle beam that is reduced in energy by the energy degrader.

19 Claims, 8 Drawing Sheets

CHARGED PARTICLE BEAM IRRADIATION APPARATUS

RELATED APPLICATIONS

The content of Japanese Patent Application No. 2020-060893, on the basis of which priority benefits are claimed in an accompanying application data sheet, is in its entirety incorporated herein by reference.

BACKGROUND

Technical Field

Certain embodiments of the present invention relate to a charged particle beam irradiation apparatus.

Description of Related Art

For example, a charged particle beam irradiation apparatus illustrated in the related art is known. The charged particle beam irradiation apparatus includes an accelerator that accelerates charged particles to generate a charged particle beam, a rotary unit that is rotatable around a rotation axis, an irradiator that performs the irradiation of the charged particle beam generated by the accelerator, and a transporter that transports the charged particle beam from the accelerator to the irradiator. The charged particle beam irradiation apparatus illustrated in FIG. 4 of the related art includes an energy selection system (ESS), which selects an energy of the charged particle beam, above the irradiator. The energy selection system in the related art includes a degrader that reduces the energy of the charged particle beam, a pair of bending electromagnets and an aperture that limit the momentum width of the charged particle beam, and a collimator.

SUMMARY

According to an embodiment of the present invention, there is provided a charged particle beam irradiation apparatus that performs irradiation of a charged particle beam, the apparatus including: an accelerator that accelerates a charged particle to generate the charged particle beam; an irradiator that includes a rotary unit rotatable around a rotation axis, and performs irradiation of the charged particle beam generated by the accelerator; and a transporter that includes a degrader provided outside the irradiator to reduce an energy of the charged particle beam generated by the accelerator, and transports the charged particle beam, which is generated by the accelerator, to the irradiator. The transporter transports the charged particle beam to the irradiator while maintaining an energy distribution of the charged particle beam that is reduced in energy by the degrader.

DETAILED DESCRIPTION

Here, in the configuration illustrated in FIG. 4 of the related art, the Bragg peak of the charged particle beam is made thin by the aperture. For this reason, the number of energies of the charged particle beam required to form a spread out Bragg peak is increased, and the number of times of switching the energy of the charged particle beam is increased, so that the time of irradiation of the charged particle beam is lengthened, which is a problem.

Therefore, it is desirable to provide a charged particle beam irradiation apparatus capable of shortening the time of irradiation of a charged particle beam.

In the charged particle beam irradiation apparatus according to an embodiment of the present invention, the degrader which reduces the energy of the charged particle beam is disposed in the transporter outside the irradiator. The transporter transports the charged particle beam to the irradiator while maintaining the energy distribution of the charged particle beam that is reduced in energy by the degrader. Accordingly, the transporter can transport the charged particle beam from the degrader to the irradiator without being provided with an energy selection system that selects an energy in a specific range among the energies of the charged particle beam. Therefore, as compared to when the energy selection system is provided, the Bragg peak of the charged particle beam is thicker, the number of energies of the charged particle beam required to form a spread out Bragg peak is further reduced, and the number of times of switching the energy of the charged particle beam is further reduced. As described above, the time of irradiation of the charged particle beam can be shortened.

In the charged particle beam irradiation apparatus according to an embodiment of the present invention, the transporter may include a collimator that is provided between the degrader and the irradiator to adjust a shape, a size, and divergence of the charged particle beam. In this case, the collimator can adjust the shape and divergence of the charged particle beam that has passed through the degrader, and the charged particle beam can be transported from the degrader to the irradiator while the energy distribution of the charged particle beam is maintained.

In the charged particle beam irradiation apparatus according to an embodiment of the present invention, the transporter may have a hole diameter that allows the charged particle beam, which is reduced in energy by the degrader, to pass through the transporter. In this case, the transporter can transport the charged particle beam from the degrader to the irradiator while maintaining the energy distribution of the charged particle beam without selecting an energy in a specific range for the charged particle beam.

In the charged particle beam irradiation apparatus according to an embodiment of the present invention, the degrader may reduce the energy of the charged particle beam, which is generated by the accelerator, such that a momentum dispersion of the charged particle beam is less than 6%. The further the energy of the charged particle beam is reduced by the degrader, the larger the energy distribution of the charged particle beam is spread. Since the degrader causes the momentum dispersion of the charged particle beam to be less than 6%, the spread of the energy distribution of the charged particle beam can be suppressed. In this case, the transporter can transport the charged particle beam from the degrader to the irradiator while maintaining the energy distribution of the charged particle beam without selecting an energy in a specific range for the charged particle beam.

In the charged particle beam irradiation apparatus according to an embodiment of the present invention, the irradiator may further include a scanning electromagnet that scans the charged particle beam, a duct through which the charged particle beam scanned by the scanning electromagnet passes, and a monitor that detects the charged particle beam which has passed through the duct. An inside of the duct may be exposed to an atmosphere. In this case, the charged particle beam passing through the duct from the scanning electromagnet toward the monitor is scattered by the atmosphere (air) inside the duct. Accordingly, a collapse of the symmetry of the cross-sectional beam shape of the charged particle beam is suppressed. Therefore, the irradiator can irradiate a proper range with the charged particle beam.

In the charged particle beam irradiation apparatus according to an embodiment of the present invention, the transporter may include a hexapole magnet or a bending magnet including hexapole components, which causes the charged particle beam to converge to trim a momentum dispersion of the charged particle beam. In this case, the transporter can trim the shape of the charged particle beam according to the energy distribution of the charged particle beam passing therethrough, and can properly transport the charged particle beam from the accelerator to the irradiator.

According to an embodiment of the present invention, it is possible to provide the charged particle beam irradiation apparatus capable of shortening the time of irradiation of the charged particle beam.

Hereinafter, a charged particle beam irradiation apparatus according to an exemplary embodiment of the present invention will be described with reference to the drawings. Incidentally, in the description of the drawings, the same components are denoted by the same reference signs, and duplicated description will be omitted. In the present embodiment, a charged particle beam treatment apparatus will be described as an example of the charged particle beam irradiation apparatus. The charged particle beam treatment apparatus is applied to, for example, cancer treatment, and is an apparatus that irradiates a tumor (irradiation target) in the body of a patient with a charged particle beam such as a proton beam.

Figure 1:
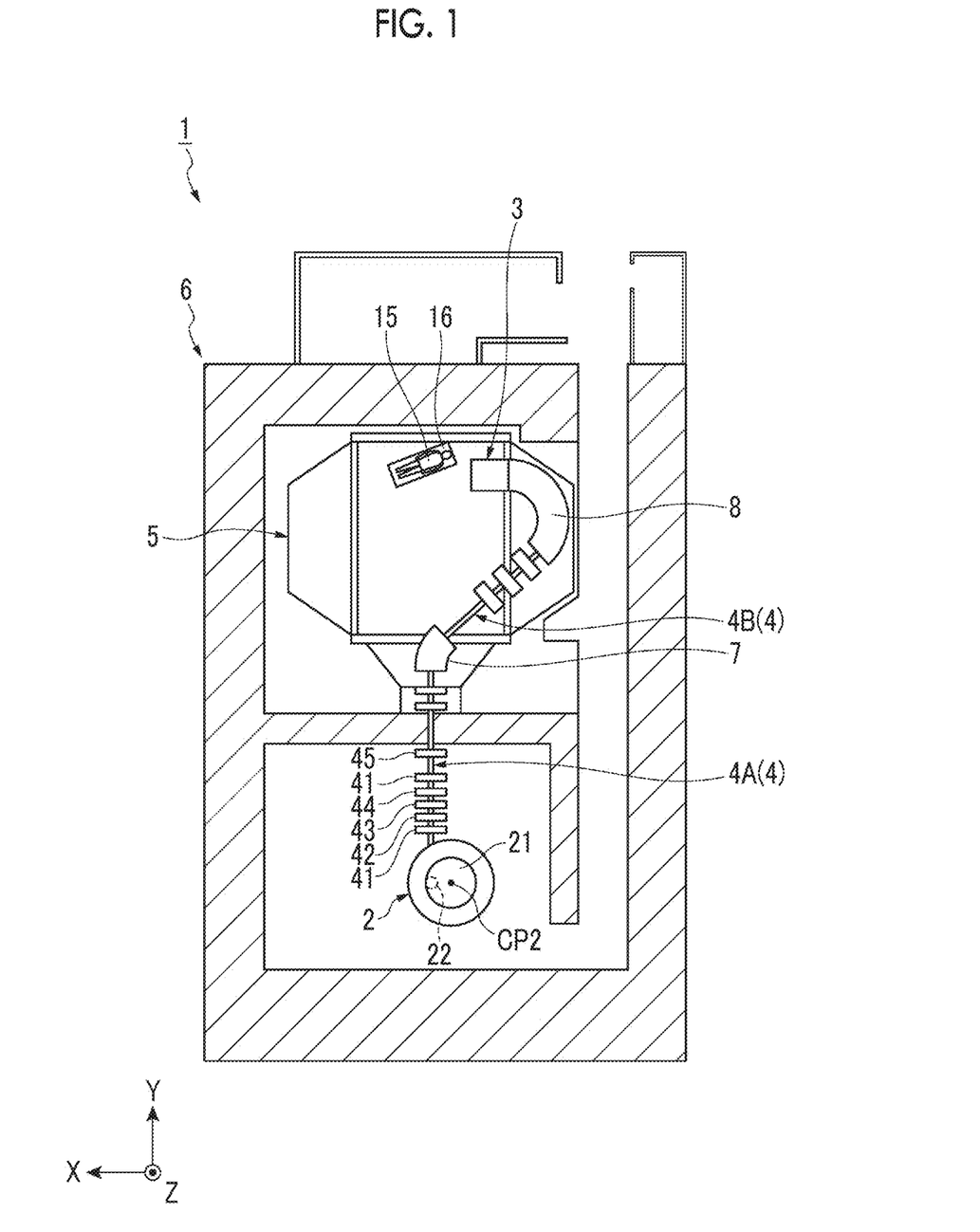
FIG. 1 is a layout view of a charged particle beam irradiation apparatus according to one embodiment of the present invention in a plan view.

A schematic configuration of the charged particle beam irradiation apparatus of the present embodiment will be described. FIG. 1 is a layout view of the charged particle beam irradiation apparatus according to one embodiment of the present invention in a plan view. As illustrated in FIG. 1, a charged particle beam irradiation apparatus 1 includes an accelerator 2 that generates a charged particle beam, an irradiator 3 that is rotatable and irradiates a patient 15 on a treatment table 16 with the charged particle beam in an arbitrary direction, and a transporter 4 that transports the charged particle beam, which is generated by the accelerator 2, to the irradiator 3. In addition, each of the devices of the charged particle beam irradiation apparatus 1 is installed in, for example, a room of a building 6 with one story.

The irradiator 3 is attached to a gantry 5 (one example of a rotary unit) provided to surround the treatment table 16. The irradiator 3 can be rotated around the treatment table 16 by the gantry 5. The gantry 5 is rotatable around a rotation axis. The transporter 4 includes an external path 4A that transports the charged particle beam from the accelerator 2 to the gantry 5, and an internal path 4B that transports the charged particle beam to the irradiator 3 inside the gantry 5. The external path 4A enters the gantry 5 from a rear end side of the gantry 5. Then, in the internal path 4B, the trajectory of the charged particle beam is changed to an outer periphery side by a bending electromagnet 7, and then the trajectory of the charged particle beam is greatly bent by a bending electromagnet 8 (one example of a hexapole magnet or a bending magnet including hexapole components) to enter the irradiator 3 from the outer periphery side.

Figure 2:
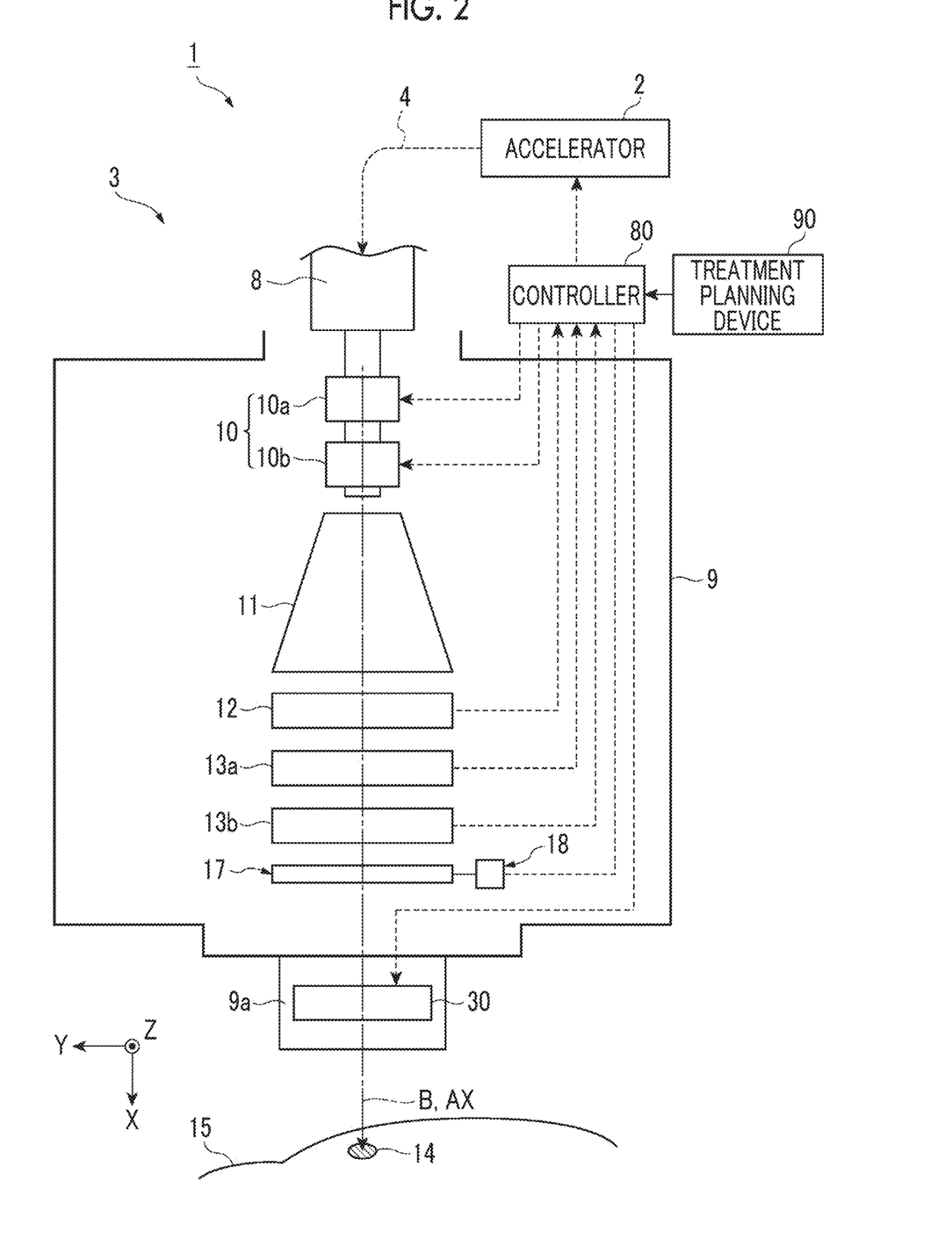
FIG. 2 is a schematic configuration view of the vicinity of an irradiator of the charged particle beam irradiation apparatus of FIG. 1.

FIG. 2 is a schematic configuration view of the vicinity of the irradiator of the charged particle beam irradiation apparatus of FIG. 1. Incidentally, in the following description, the terms such as an "X-axis direction", a "Y-axis direction", and a "Z-axis direction" will be used. The "X-axis direction" is a direction along a base axis AX of the irradiator 3, and is a depth direction of irradiation of a charged particle beam B. Incidentally, the details of the "base axis AX" will be described later. FIG. 2 illustrates a mode in which the irradiation of the charged particle beam B is performed along the base axis AX. The "Y-axis direction" is one direction in a plane perpendicular to the X-axis direction. The "Z-axis direction" is a direction perpendicular to the Y-axis direction in the plane perpendicular to the X-axis direction.

A detailed configuration of the charged particle beam irradiation apparatus 1 according to the present embodiment will be described with reference to FIGS. 1 and 2. The charged particle beam irradiation apparatus 1 is an irradiation apparatus according to a scanning method. Incidentally, the scanning method is not particularly limited, and line scanning, raster scanning, spot scanning, or the like may be adopted. The charged particle beam irradiation apparatus 1 includes a controller 80 and a treatment planning device 90 in addition to the accelerator 2, the irradiator 3, and the transporter 4.

The accelerator 2 is a device that accelerates charged particles to generate the charged particle beam B of an energy set in advance. The charged particle beam B generated by the accelerator 2 is guided to the irradiator 3 through a trajectory formed by the transporter 4. Examples of the accelerator 2 include a cyclotron, a synchrocyclotron, a linear accelerator, and the like. The cyclotron from which the charged particle beam B of an energy set in advance is exited is adopted as the accelerator 2 in the present embodiment. The accelerator 2 includes a vacuum chamber 21 that accelerates ions (charged particles) while causing the ions to orbit on an acceleration plane thereinside, and an ion source (not illustrated) that supplies ions into the vacuum chamber 21. The vacuum chamber 21 communicates with the external path 4A of the transporter 4. The charged particle beam B orbiting inside the vacuum chamber 21 is extracted from an orbit trajectory by a deflector 22, and is supplied to the external path 4A of the transporter 4. Incidentally, the acceleration plane of the accelerator 2 is widened in a horizontal direction (the X-axis direction and the Y-axis direction). The center of the acceleration plane is a center point CP2 (refer to FIG. 1). A center line of the vacuum chamber 21, which extends in the Z-axis direction, passes through the center point CP2. The accelerator 2 is connected to the controller 80, and current to be supplied is controlled.

As illustrated in FIG. 1, the transporter 4 includes an energy degrader 43 (one example of a degrader) that is provided outside the irradiator 3 to reduce the energy of the charged particle beam B generated by the accelerator 2, and transports the charged particle beam B, which is generated by the accelerator 2, to the irradiator 3. In addition, the transporter 4 includes a collimator 44 that is provided between the energy degrader 43 and the irradiator 3 to adjust the shape, size, and divergence of the charged particle beam B. The external path 4A of the transporter 4 includes a quadrupole electromagnet 41, a steering electromagnet 42, the energy degrader 43, the collimator 44, the quadrupole electromagnet 41, and a beam stopper 45 in order from an upstream side. The quadrupole electromagnet 41 is an electromagnet that causes the charged particle beam B to converge to trim the shape of the charged particle beam. The steering electromagnet 42 is an electromagnet that corrects the trajectory of the charged particle beam. The energy degrader 43 is a mechanism that reduces the energy of the charged particle beam overall to adjust the range. The collimator 44 forms the shape of the charged particle beam, adjusts the size of the charged particle beam, and adjusts the divergence of the charged particle beam. The beam stopper 45 is a mechanism that performs switching between the exit and the stop of the charged particle beam. The internal path 4B of the transporter 4 includes the bending electromagnets 7 and 8 as described above.

The irradiator 3 performs the irradiation of the charged particle beam B generated by the accelerator 2. Specifically, as illustrated in FIG. 2, the irradiator 3 irradiates a tumor (irradiation target) 14 inside the body of the patient 15 with the charged particle beam B. The charged particle beam B is obtained by accelerating charged particles at a high speed, and examples of the charged particle beam B include a proton beam, a baryon (heavy ion) beam, a particle beam, and the like. Specifically, the irradiator 3 is a device that irradiates the tumor 14 with the charged particle beam B exited from the accelerator 2 which accelerates the charged particles generated by the ion source (not illustrated) and is transported by the transporter 4. The irradiator 3 includes a scanning electromagnet 10, a duct 11, a dose monitor 12 (one example of a monitor), position monitors 13a and 13b (one example of a monitor), a collimator 17, and a snout degrader 30. The scanning electromagnet 10, the duct 11, the monitors 12, 13a, and 13b, the collimator 17, and the snout degrader 30 are accommodated in an irradiation nozzle 9 as an accommodation body. In such a manner, the components are accommodated in the irradiation nozzle 9 to form the irradiator 3. Incidentally, in addition to the above-described components, a hexapole magnet or a bending magnet including hexapole components, and a profile monitor may be provided upstream of the scanning electromagnet 10. In addition, the dose monitor 12 and the position monitors 13a and 13b may be omitted.

The scanning electromagnet 10 includes a Y-axis direction scanning electromagnet 10a and a Z-axis direction scanning electromagnet 10b. The Y-axis direction scanning electromagnet 10a and the Z-axis direction scanning electromagnet 10b each are formed of a pair of electromagnets, and change a magnetic field between the pair of electromagnets according to current supplied from the controller 80, to scan the charged particle beam B passing between the electromagnets. In the scanning electromagnet 10, the Y-axis direction scanning electromagnet 10a scans the charged particle beam B in the Y-axis direction, and the Z-axis direction scanning electromagnet 10b scans the charged particle beam B in the Z-axis direction. The scanning electromagnets 10 are disposed closer to a downstream side of the charged particle beam B on the base axis AX in order than the accelerator 2. Incidentally, the scanning electromagnet 10 scans the charged particle beam B such that the irradiation of the charged particle beam B is performed along a scanning path planned in advance by the treatment planning device 90.

The duct 11 is disposed downstream of the scanning electromagnet 10 on the base axis AX. The duct 11 guides the charged particle beam B, which is scanned by the scanning electromagnet 10, to the dose monitor 12 disposed downstream of the duct 11. The duct 11 has, for example, a truncated cone shape that is widened as the duct 11 extends from an upstream side toward a downstream side of the base axis AX. The duct 11 is penetrated along the base axis AX. The inside of the duct 11 is exposed to the atmosphere. Namely, the duct 11 contains the atmosphere (air) thereinside. The atmosphere (air) contains, for example, nitrogen and oxygen. The inside of the duct 11 is exposed to, for example, the atmosphere. In this case, the entire inside of the irradiation nozzle 9 may be exposed to the atmosphere, or only the inside of the duct 11 may be configured to be exposed to the atmosphere.

The dose monitor 12 is disposed downstream of the duct 11 on the base axis AX. The position monitors 13a and 13b detect and monitor the beam shape and position of the charged particle beam B. The position monitors 13a and 13b are disposed closer to the downstream side of the charged particle beam B on the base axis AX in order than the dose monitor 12. Each of the monitors 12, 13a, and 13b outputs a detected detection result to the controller 80.

The snout degrader 30 reduces the energy of the charged particle beam B passing therethrough, to shift the range of the charged particle beam B. In the present embodiment, the snout degrader 30 is provided at a tip part 9a of the irradiation nozzle 9. Incidentally, the tip part 9a of the irradiation nozzle 9 is an end part on the downstream side of the charged particle beam B. The snout degrader 30 has, for example, a water equivalent thickness of approximately 10 cm.

The collimator 17 is a member that is provided closer to the downstream side of the charged particle beam B than at least the scanning electromagnet 10 to block a part of the charged particle beam B, and to allow a part of the charged particle beam B to pass therethrough. Here, the collimator 17 is provided downstream of the position monitors 13a and 13b. The collimator 17 is connected to a collimator drive unit 18 that moves the collimator 17.

The controller 80 is formed of, for example, a CPU, a ROM, a RAM, and the like. The controller 80 controls the accelerator 2, the scanning electromagnet 10, and the collimator drive unit 18 based on the detection result output from each of the monitors 12, 13a, and 13b.

In addition, the controller 80 of the charged particle beam irradiation apparatus 1 is connected to the treatment planning device 90 that performs treatment planning for charged particle beam treatment. The treatment planning device 90 measures the tumor 14 of the patient 15 using a CT or the like before treatment, and plans a radiation dose distribution (radiation dose distribution of the charged particle beam, of which the irradiation is to be performed) at each position in the tumor 14. Specifically, the treatment planning device 90 creates a treatment planning map for the tumor 14. The treatment planning device 90 transmits the created treatment planning map to the controller 80. In the treatment planning map created by the treatment planning device 90, it is planned what scanning path is drawn by the charged particle beam B.

When the irradiation of the charged particle beam B is performed by the scanning method, the tumor 14 is imaginarily divided into a plurality of layers in the X-axis direction, and the scanning and irradiation of one layer with the charged particle beam are performed along the scanning path determined in the treatment planning. Then, after the irradiation of the one layer with the charged particle beam B is completed, the next adjacent layer is irradiated with the charged particle beam B.

When the irradiation of the charged particle beam is performed by the scanning method, first, the charged particle beam B is exited from the accelerator 2. The charged particle beam B exited is scanned along the scanning path determined in the treatment planning by controlling of the scanning electromagnet 10. Accordingly, the tumor 14 is irradiated with the charged particle beam B while being scanned in an irradiation range in one layer set in the Z-axis direction. When the irradiation of one layer is completed, the next layer is irradiated with the charged particle beam B.

Figure 3A:
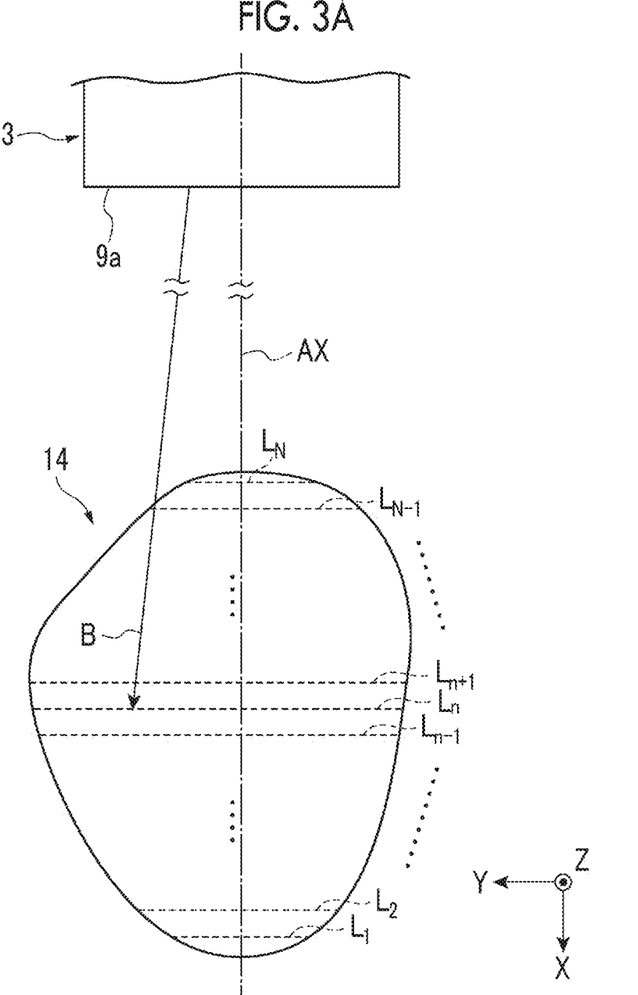
FIGS. 3A and 3B are views illustrating layers set for a tumor.
Figure 3B:
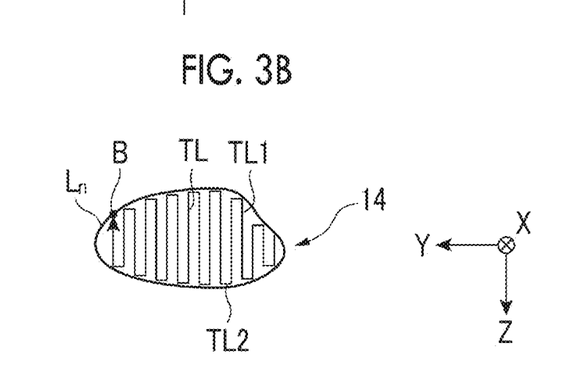

A charged particle beam irradiation image of the scanning electromagnet 10 according to control of the controller 80 will be described with reference to FIGS. 3A and 3B. FIGS. 3A and 3B are views illustrating layers set for the tumor. FIG. 3A illustrates the irradiation target that is imaginarily sliced into a plurality of layers in the depth direction, and FIG. 3B illustrates scanning lines of the charged particle beam in one layer when seen in the depth direction.

As illustrated in FIG. 3A, the irradiation target is imaginarily sliced into the plurality of layers in the depth direction of irradiation, and in the present example, is imaginarily sliced into N layers, specifically, a layer $L_1$, a layer $L_2$, . . . a layer $L_{n-1}$, a layer $L_n$, a layer $L_{n+1}$, . . . a layer $L_{N-1}$, and a layer $L_N$ in order from deep (range of the charged particle beam B is long) layers. In addition, as illustrated in FIG. 3B, while the charged particle beam B draws a beam trajectory along a scanning path TL, the irradiation of the charged particle beam B is continuously performed along the scanning path IL of the layer $L_n$ in the case of continuous scanning (line scanning or raster scanning), and a plurality of irradiation spots of the layer $L_n$ are irradiated with the charged particle beam B in the case of spot scanning. The irradiation of the charged particle beam B is performed along a scanning path TL1 extending in the Z-axis direction, the charged particle beam B is slightly shifted in the Y-axis direction along a scanning path TL2, and the irradiation of the charged particle beam B is performed along the adjacent scanning path TL1. In such a manner, the charged particle beam B exited from the irradiator 3 controlled by the controller 80 moves on the scanning path TL.

Figure 4A:
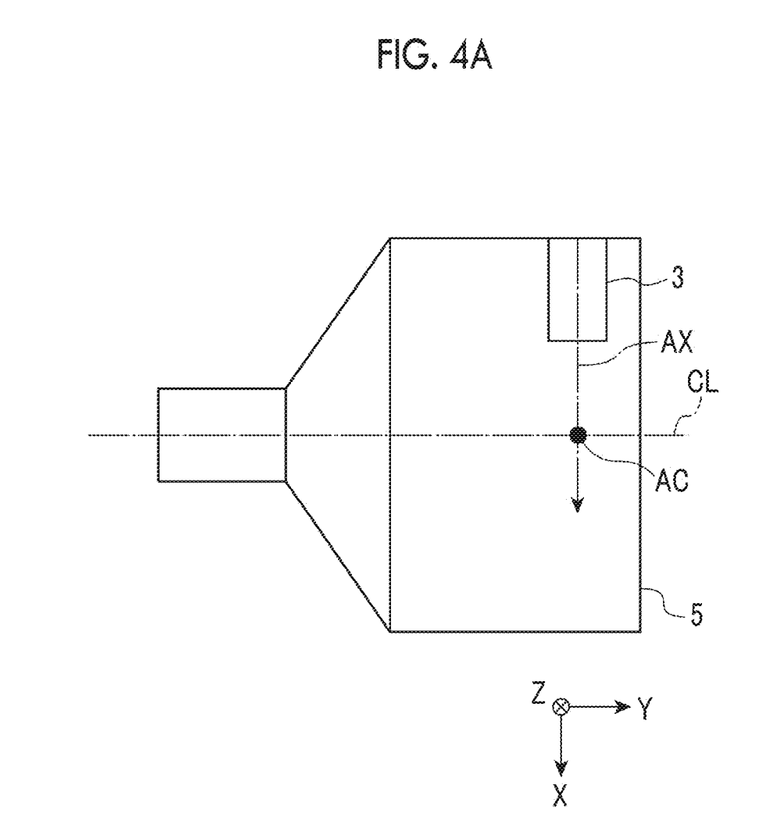
FIGS. 4A and 4B are schematic views for describing a base axis of the irradiator.
Figure 4B:
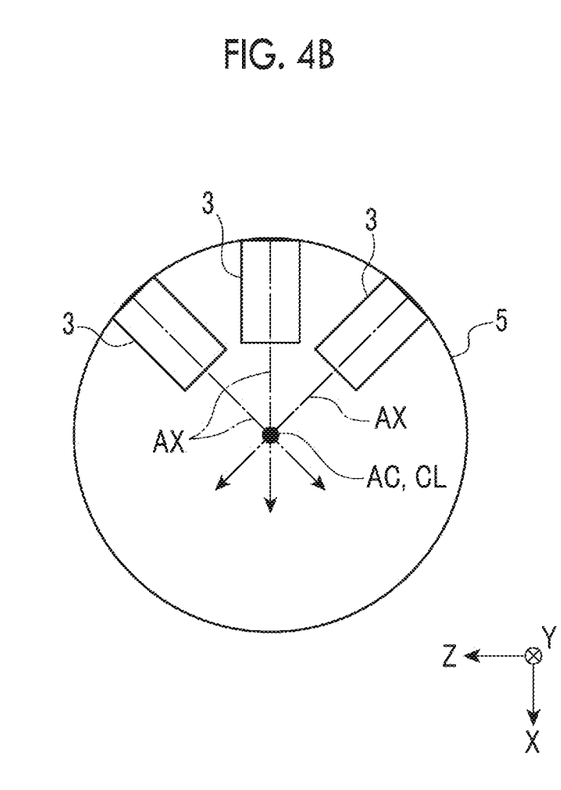

FIGS. 4A and 4B are schematic views for describing the base axis of the irradiator. The "base axis AX" of the irradiator 3 will be described with reference to FIGS. 4A and 4B. The base axis AX is an imaginary reference line that serves as a reference when the irradiator 3 performs the irradiation of the charged particle beam B. Even when the treatment planning device 90 creates a scanning pattern in performing treatment planning, the treatment planning is performed with reference to the base axis AX. For example, when the layers illustrated in FIG. 3A are set, each of the layers has a plane perpendicular to the base axis AX. In addition, even when the amount of movement in the Y-axis direction and the amount of movement in the Z-axis direction are set, the position of the base axis AX is used as a reference. As illustrated in FIG. 4A, the base axis AX is perpendicular to a center line CL of the gantry 5, and passes through the center line CL. The base axis AX passes through an isocenter AC on the center line CL of the gantry 5. As illustrated in FIG. 4B, when the gantry 5 rotates to cause the irradiator 3 to rotate around the isocenter AC, the base axis AX passes through the isocenter AC on the gantry 5 regardless of the position of the irradiator 3. Incidentally, an XYZ coordinate system is a relative coordinate system that changes depending on the direction of the base axis AX. FIGS. 4A and 4B illustrate the XYZ coordinate system in a state where the base axis AX extends in a vertical direction. In addition, FIG. 1 described above illustrates a state where the base axis AX extends in a horizontal direction to illustrate the form of the irradiator 3. Therefore, FIG. 1 illustrates an XYZ coordinate system corresponding to the state.

Next, the energy distribution of the charged particle beam B, of which the irradiation is performed in the charged particle beam irradiation apparatus 1 according to the present embodiment, will be described with reference to FIG. 5.

Figure 5:
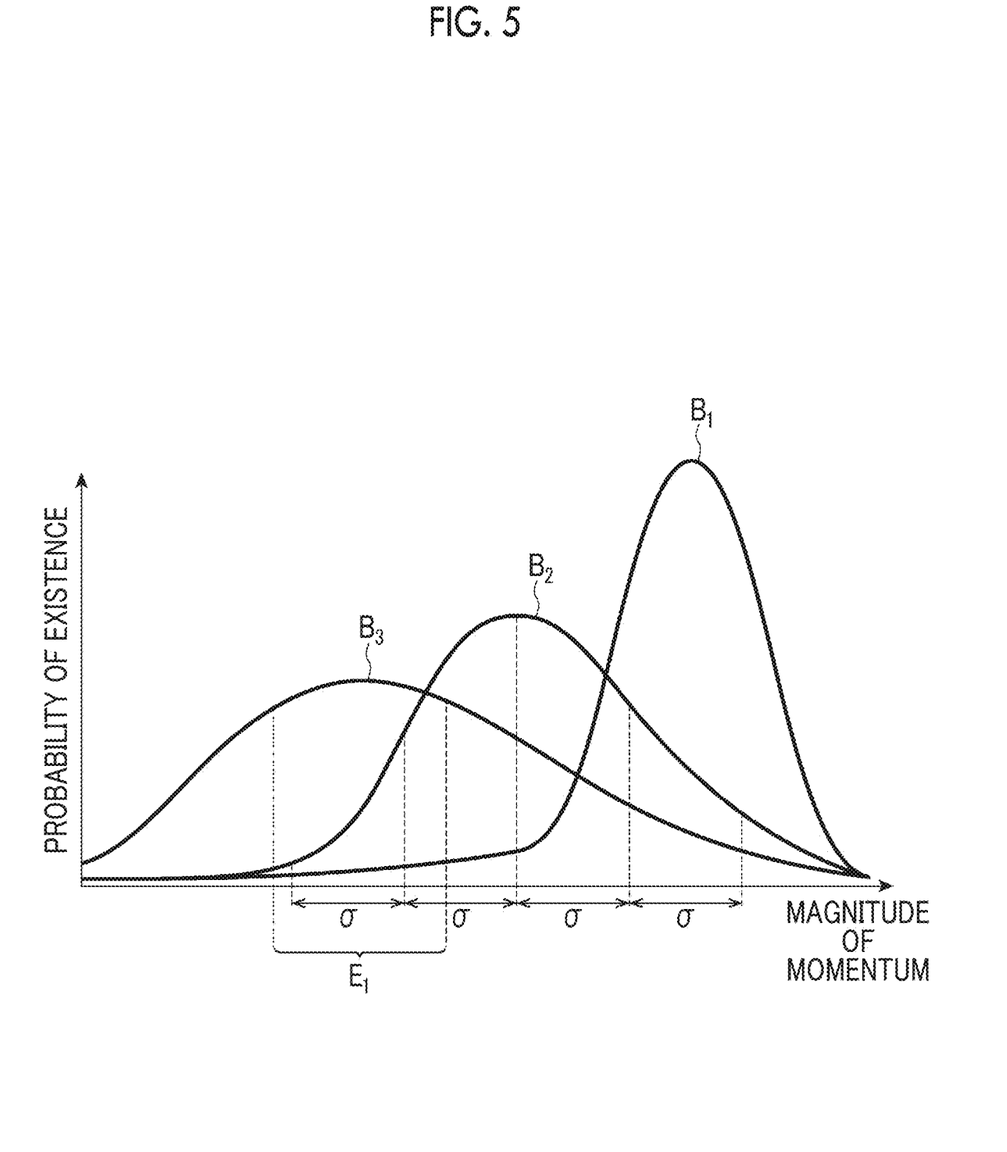
FIG. 5 is a graph illustrating the energy distributions of charged particle beams generated in the charged particle beam irradiation apparatus according to one embodiment of the present invention.

FIG. 5 is a graph illustrating the energy distributions of charged particle beams generated in the charged particle beam irradiation apparatus according to one embodiment of the present invention. The vertical axis of the graph illustrated in FIG. 5 indicates the probability of existence, and the horizontal axis indicates the magnitude of momentum. Among the charged particle beams B, a charged particle beam $B_1$ generated by the accelerator 2 has, for example, approximately 230 MeV. In the energy distribution of the charged particle beam $B_1$, the spread of momentum is small. Namely, the probability of existence of the charged particle beam $B_1$ having momentum away from the average value of momentum of the charged particle beam $B_1$ is remarkably smaller than the probability of existence of the charged particle beam $B_1$ in the vicinity of the average value of the momentum of the charged particle beam $B_1$. Here, the expression that the spread of momentum is large means that the probability of existence at the average value of momentum is small, and the probability of existence of the charged particle beam having various momentum is large. In the charged particle beam irradiation apparatus 1 of the present embodiment, among the charged particle beams B, a charged particle beam $B_2$, into which the charged particle beam $B_1$ exited from the accelerator 2 is reduced in energy to be transformed by the energy degrader 43, has a larger spread of momentum than that of the charged particle beam $B_1$ due to being reduced in energy. As the spread of momentum of the charged particle beam $B_2$, the momentum dispersion of the charged particle beam $B_2$ is less than 6%. In addition, the momentum dispersion of the charged particle beam $B_2$ may be 5% or less, or may be 4% or less, 3% or less, or 2% or less. In this case, the charged particle beam $B_2$ has, for example, 110 MeV. Incidentally, the momentum dispersion is the value of dispersion of momentum corresponding to the energy of the charged particle beam B.

The transporter 4 transports the charged particle beam $B_2$ to the irradiator 3 while maintaining the energy distribution of the charged particle beam $B_2$ that is reduced in energy by the energy degrader 43. Specifically, in the transporter 4, a member such as a momentum resolving aperture (for example, a momentum resolving aperture 157 illustrated in FIG. 7) which adjusts the energy distribution is not provided at any location in the external path 4A and the internal path 4B. Incidentally, after the charged particle beam $B_2$ passes through the energy degrader 43, the energy distribution of the charged particle beam $B_2$ is affected for the first time by the snout degrader 30 inside the irradiator 3. Therefore, even inside the irradiator 3, a member such as a momentum resolving aperture which affects the energy distribution is not provided in a path upstream of the snout degrader 30. Incidentally, when the transporter 4 includes a plurality of stages of the energy degraders 43, the transporter 4 maintains the energy distribution of the charged particle beam $B_2$ which has passed through the energy degrader 43 disposed on the downstream-most side.

The larger the spread of momentum of the charged particle beam B is (the smaller the energy is), the larger the beam diameter of the charged particle beam B passing through the transporter 4 is. For this reason, the beam diameter of the charged particle beam $B_2$ is larger than the beam diameter of the charged particle beam $B_1$. The transporter 4 has a hole diameter that allows the charged particle beam $B_2$, which is reduced in energy by the energy degrader 43, to pass therethrough. The transporter 4 has a hole diameter at least on the downstream side of the energy degrader 43, which allows the charged particle beam $B_2$ to pass therethrough. Accordingly, the transporter 4 can transport the charged particle beam $B_2$ from the accelerator 2 toward the gantry 5 without selecting an energy of the charged particle beam $B_2$. In this case, in the charged particle beam irradiation apparatus 1, for example, the external path 4A of the transporter 4 can extend linearly from the accelerator 2 toward the gantry 5.

Since the charged particle beam $B_2$ inside the transporter 4 has a larger spread of momentum than that of the charged particle beam $B_1$, and the trajectory slightly differs depending on momentum, there is a possibility that the cross-sectional beam shape of the charged particle beam $B_2$ is asymmetric. In order to secure the symmetry of the cross-sectional beam shape of the charged particle beam $B_2$, the transporter 4 includes a hexapole magnet or a bending magnet including hexapole components, which causes the charged particle beam $B_2$ to converge to trim the shape of the charged particle beam $B_2$, in addition to the collimator 44 that adjusts the shape, size, and divergence of the charged particle beam $B_2$. For example, the bending electromagnet 8 provided in the internal path 4B of the transporter 4 is a bending magnet including hexapole components.

Figure 6A:
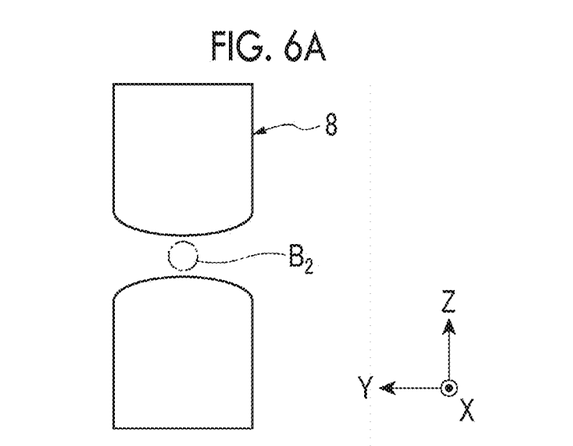
FIG. 6A is a schematic configuration view of a bending magnet, which includes hexapole components each having a convex shape, in a transporter of the charged particle beam irradiation apparatus according to one embodiment of the present invention.
Figure 6B:
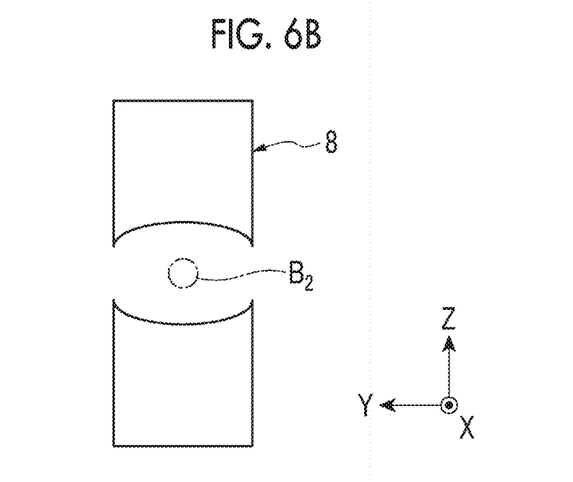
FIG. 6B is a schematic configuration view of a bending magnet, which includes hexapole components each having a concave shape, in the transporter of the charged particle beam irradiation apparatus according to one embodiment of the present invention.
Figure 6C:
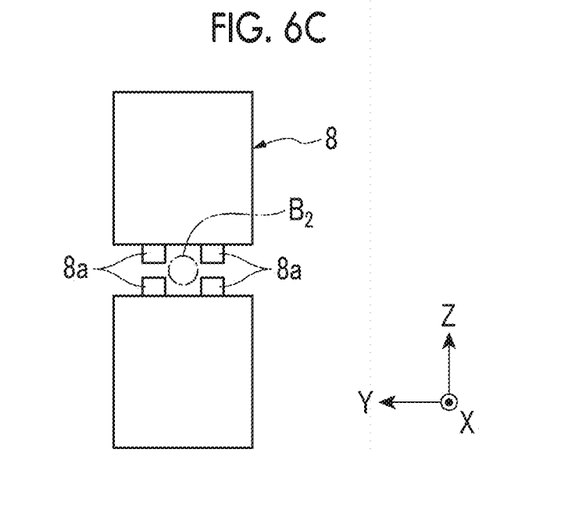
FIG. 6C is a schematic configuration view of a bending magnet, which includes hexapole components including auxiliary coils, in the transporter of the charged particle beam irradiation apparatus according to one embodiment of the present invention.

As illustrated in FIGS. 6A to 6C, the bending electromagnet 8 can have various shapes to output hexapole components. FIGS. 6A, 6B, and 6C are schematic cross-sectional views in a cross section perpendicular to the path of the charged particle beam $B_2$. FIG. 6A is a schematic configuration view of a bending magnet, which includes hexapole components each having a convex shape, in the transporter of the charged particle beam irradiation apparatus according to one embodiment of the present invention.

As illustrated in FIG. 6A, the bending electromagnet 8 has, for example, a shape that bulges convexly toward a space through which the charged particle beam $B_2$ passes. FIG. 6B is a schematic configuration view of a bending magnet, which includes hexapole components each having a concave shape, in the transporter of the charged particle beam irradiation apparatus according to one embodiment of the present invention. As illustrated in FIG. 6B, the bending electromagnet 8 may have, for example, a shape that is concavely recessed toward the space through which the charged particle beam $B_2$ passes. FIG. 6C is a schematic configuration view of a bending magnet, which includes hexapole components including auxiliary coils, in the transporter of the charged particle beam irradiation apparatus according to one embodiment of the present invention. As illustrated in FIG. 6C, the bending electromagnet 8 may include, for example, auxiliary coils 8a in the space through which the charged particle beam $B_2$ passes.

As described above, since the bending electromagnet 8 is a bending magnet including hexapole components, the bending electromagnet 8 can correct the trajectory that differs depending on momentum, and secure the symmetry of the cross-sectional beam shape of the charged particle beam $B_2$. The transporter 4 can trim the shape of the charged particle beam $B_2$ according to the energy distribution of the charged particle beam $B_2$ passing therethrough, and can properly transport the charged particle beam $B_2$ from the accelerator 2 to the irradiator 3. In the transporter 4, the bending electromagnet 7 may also be a hexapole magnet or a bending magnet including hexapole components.

Since the charged particle beam $B_2$ which reaches the irradiator 3 from the transporter 4 passes through the duct 11 exposed to the atmosphere (containing air inside), the charged particle beam B is scattered. Since the duct 11 is exposed to the atmosphere (contains air), the charged particle beam $B_2$ is more scattered, and the symmetry of the cross-sectional beam shape of the charged particle beam $B_2$ is further secured than in a state where the inside of the duct is in a vacuum state or is filled with rare gas and does not contain air.

Next, the effects of the charged particle beam irradiation apparatus 1 according to the present embodiment will be described in comparison with those of a charged particle beam irradiation apparatus 100 according to Comparative Example 1. In Comparative Example 1, the functions of the apparatus, which have the same names but only different signs, are the same as those of the embodiment.

Figure 7:
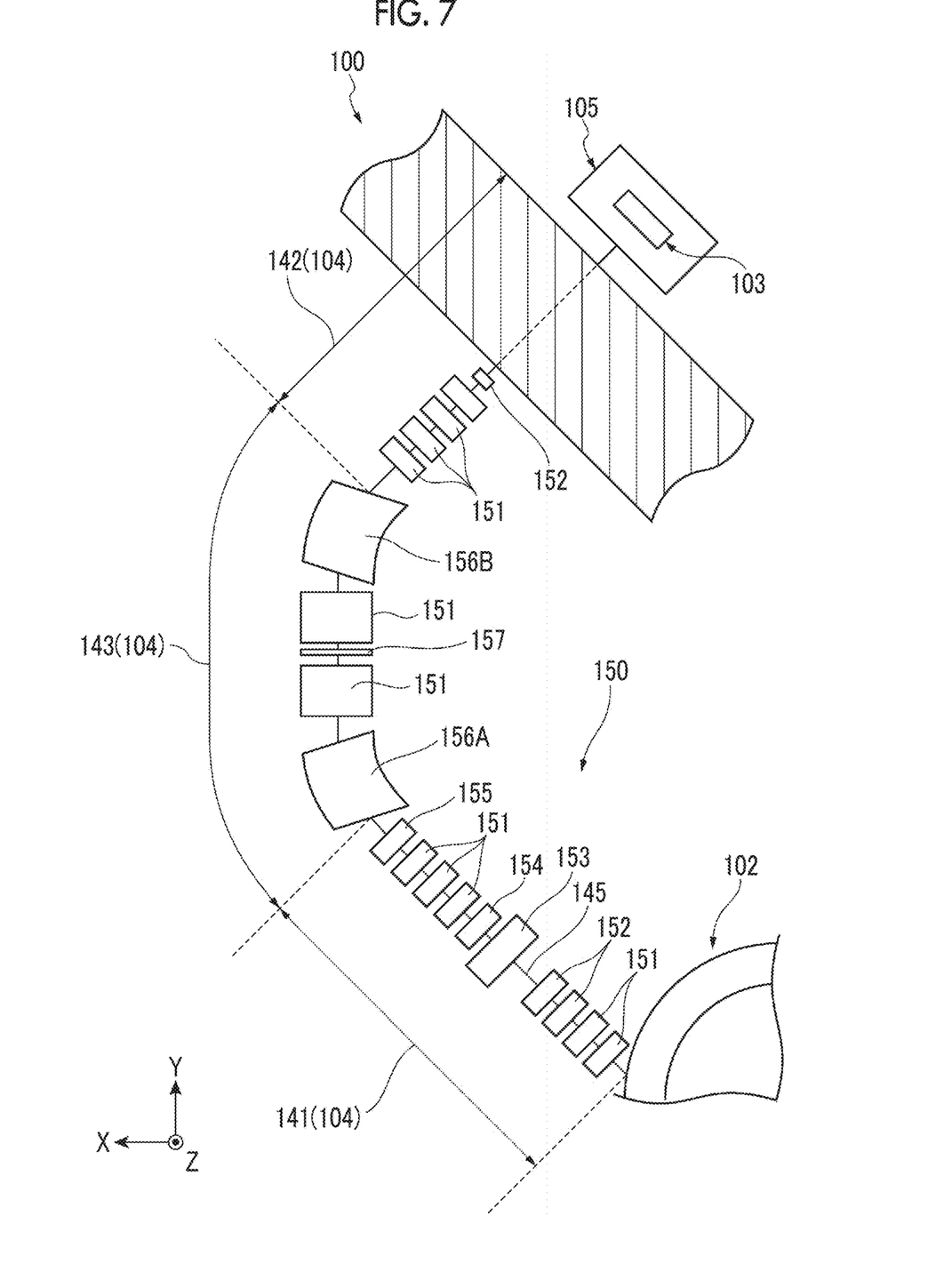
FIG. 7 is an enlarged view illustrating a configuration of an energy selection system provided in a transporter of a charged particle beam irradiation apparatus according to Comparative Example 1.

FIG. 7 is an enlarged view illustrating a configuration of an energy selection system provided in a transporter of the charged particle beam irradiation apparatus according to Comparative Example 1. An energy selection system 150 is a mechanism called an energy selection system (ESS). For example, unlike a configuration where a part of the ESS is mounted on an upper side of an irradiator 103, all the components of the energy selection system 150 are disposed in a space which is partitioned off by an indoor blockade wall and in which an accelerator 102 is disposed. The components of the energy selection system 150 are not disposed in a space where the irradiator 103 and a gantry 105 are disposed.

A detailed configuration of the energy selection system 150 provided in a transporter 104 will be described. Incidentally, each of the components of the energy selection system 150 is provided in a transport pipe 145 forming the transporter 104. The energy selection system 150 provided in a first linear portion 141 includes a quadrupole electromagnet 151, a steering electromagnet 152, an energy degrader 153, the quadrupole electromagnet 151, a collimator 154, and a beam stopper 155 in order from an upstream side. The quadrupole electromagnet 151 is an electromagnet that causes a charged particle beam to converge to trim the shape of the charged particle beam. The steering electromagnet 152 is an electromagnet that corrects the trajectory of the charged particle beam. The energy degrader 153 is a mechanism that reduces the energy of the charged particle beam overall to adjust the range. For example, the energy degrader 153 degrades the charged particle beam $B_1$, which is exited from the accelerator 102, into a charged particle beam $B_3$, of which the energy is reduced to 70 MeV (refer to FIG. 5). At this time, since the charged particle beam $B_3$ is reduced in energy, the charged particle beam $B_3$ has a larger spread of momentum than those of the charged particle beam $B_1$ and the charged particle beam $B_2$. As the spread of momentum of the charged particle beam $B_3$, the momentum dispersion of the charged particle beam $B_3$ is 6% or more. The collimator 154 adjusts the shape, size, and divergence of the charged particle beam. The collimator 154 forms the shape of the charged particle beam, adjusts the size of the charged particle beam, and adjusts the divergence of the charged particle beam. The beam stopper 155 is a mechanism that performs switching between the exit and the stop of the charged particle beam.

The energy selection system 150 provided in a bent portion 143 includes a bending electromagnet 156A, the quadrupole electromagnet 151, the momentum resolving aperture 157, the quadrupole electromagnet 151, and a bending electromagnet 156B in order from the upstream side. A plurality of the quadrupole electromagnets 151 may be provided in front of and behind the momentum resolving aperture 157. The bending electromagnet 156A is an electromagnet that bends the trajectory of the charged particle beam transported from the first linear portion 141. The degree of bending of the charged particle beam differs depending on energy. Therefore, when the charged particle beam is bent by the bending electromagnet 156A to pass through the momentum resolving aperture 157, a charged particle beam of a desired energy can be selected. The charged particle beam $B_3$ transported to the momentum resolving aperture 157 on the downstream side of the energy degrader 153 of the transporter 104 is brought into a state, in which energy in regions other than a region (refer to a region $E_1$ of FIG. 5) in the vicinity of the peak of the energy distribution of the charged particle beam $B_3$ is removed, by the momentum resolving aperture 157. Namely, when the charged particle beam $B_3$ passes through the momentum resolving aperture 157, the charged particle beam $B_3$ becomes a charged particle beam (hereinafter, a charged particle beam $B_4$) in the range of the region $E_1$ in the energy distribution, and is transported downstream.

Then, the bending electromagnet 156B bends the trajectory of the charged particle beam $B_4$ of a selected energy toward a second linear portion 142. The bent portion 143 includes only two sets of the bending electromagnets 156A and 156B, and does not include another set of bending electromagnets between the bending electromagnets 156A and 156B. Incidentally, when the bending electromagnets are continuously disposed, the bending electromagnets are regarded as one set of bending electromagnets. Namely, when the bending electromagnet 156A is divided into a plurality of bending electromagnets that are continuous, the bending electromagnet 156A is regarded as one set of bending electromagnets. In the bent portion 143, a region between the bending electromagnets 156A and 156B is a linear portion extending linearly, but the linear portion is shorter than the first linear portion 141.

The energy selection system 150 provided in the second linear portion 142 includes the quadrupole electromagnet 151 and the steering electromagnet 152 in order from the upstream side. Incidentally, the components of the energy selection system 150 are not provided in a portion of the second linear portion 142, the portion being embedded in the indoor blockade wall. In the charged particle beam irradiation apparatus 100 of Comparative Example 1, the inside of the duct is in a vacuum state, and the water equivalent thickness of the snout degrader is approximately 4 cm. As described above, in the charged particle beam irradiation apparatus 100 of Comparative Example 1, the charged particle beam $B_1$ generated by the accelerator 102 is reduced in energy by the energy degrader 153 to become the charged particle beam $B_3$. In the charged particle beam irradiation apparatus 100 of Comparative Example 1, the charged particle beam $B_3$, of which the energy distribution is limited to the range of the region $E_1$, is transformed into the charged particle beam $B_4$ by the momentum resolving aperture 157. In the charged particle beam irradiation apparatus 100 of Comparative Example 1, the charged particle beam $B_4$ is transported to the snout degrader.

Since the charged particle beam irradiation apparatus 100 of Comparative Example 1 selects a charged particle beam of a desired energy, the transporter 104 needs to include the bent portion 143. Since the transporter 104 is greatly curved, in the charged particle beam irradiation apparatus 100 of Comparative Example 1, the footprint of a facility required to dispose the accelerator 102, the irradiator 103, and the transporter 104 is increased, which is a problem. On the other hand, in the charged particle beam irradiation apparatus 1 of the present embodiment, since the energy selection system 150 does not need to be provided in the transporter 4, the shape of the transporter 4 can be freely changed according to an environment in which the transporter 4 is disposed, for example, the transporter 4 can be made linear. Accordingly, the charged particle beam irradiation apparatus 1 of the present embodiment can properly further reduce the footprint than the charged particle beam irradiation apparatus 100 of Comparative Example 1. In the charged particle beam irradiation apparatus 1, the size of the entire apparatus can be reduced, and the foot print can be reduced.

Figure 8A:
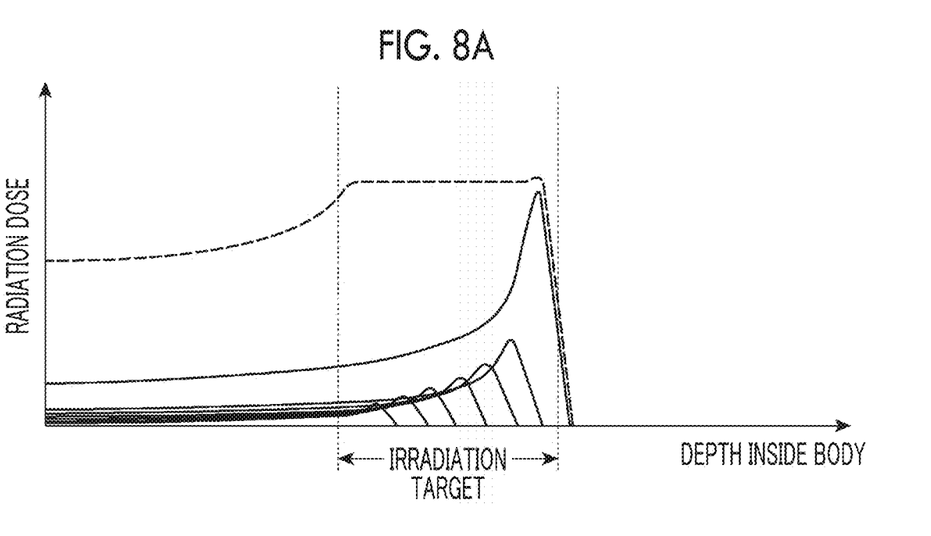
FIG. 8A is a graph illustrating the Bragg peaks of charged particle beams exited by the charged particle beam irradiation apparatus according to one embodiment of the present invention.
Figure 8B:
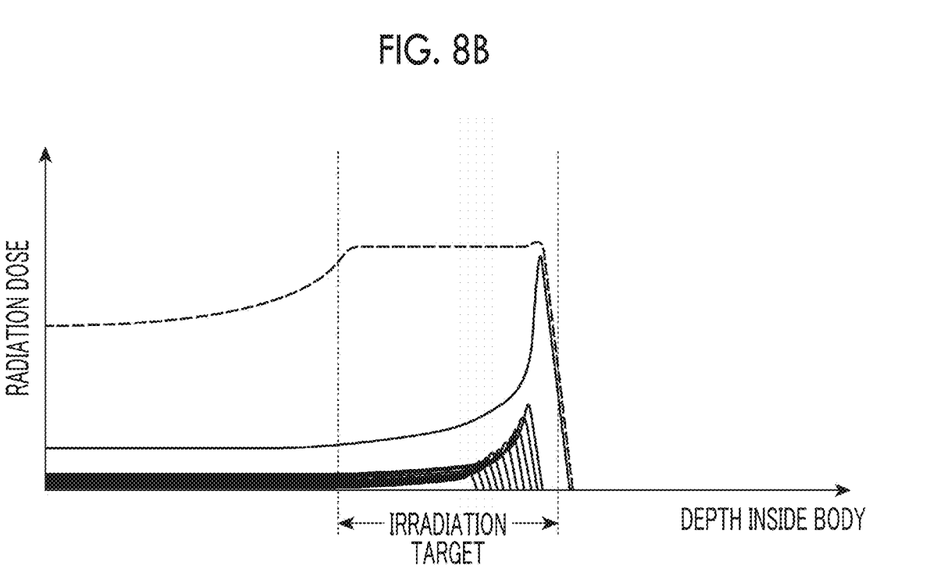
FIG. 8B is a graph illustrating the Bragg peaks of charged particle beams exited by the charged particle beam irradiation apparatus according to Comparative Example 1.

Next, the shortening of the time of irradiation will be described with reference to FIGS. 8A and 8B. FIG. 8A is a graph illustrating the Bragg peaks of charged particle beams exited by the charged particle beam irradiation apparatus according to one embodiment of the present invention. FIG. 8B is a graph illustrating the Bragg peaks of charged particle beams exited by the charged particle beam irradiation apparatus according to Comparative Example 1. Namely, FIG. 8B is a graph illustrating the Bragg peaks of the charged particle beams having a smaller energy than that of the charged particle beams exited from the charged particle beam irradiation apparatus 1 of the present embodiment. In each of the graphs of FIGS. 8A and 8B, the vertical axis indicates the radiation dose, and the horizontal axis indicates the depth inside the body. As illustrated in FIGS. 8A and 8B, the irradiation target (tumor 14) is located in a part inside the body of the patient 15. The charged particle beam irradiation apparatus 1 of the present embodiment and a charged particle beam irradiation apparatus of a modification example perform the irradiation of a plurality of the charged particle beams B showing Bragg peaks at various body depths, to form a spread out Bragg peak. Here, the Bragg peak is a characteristic of a charged particle beam that emits the maximum radiation dose and stops at a specific depth according to incident energy, and the spread out Bragg peak is formed such that the Bragg peaks corresponding to a plurality of different energies are superimposed in the depth direction of the irradiation target to be adjusted to apply a desired radiation dose to the irradiation target.

Since the charged particle beam $B_2$ of the present embodiment has a larger momentum dispersion per one charged particle beam B than that of the charged particle beam $B_4$ of Comparative Example 1 (since the energy width is larger), the Bragg peak of the charged particle beam $B_2$ of the present embodiment is thicker than the Bragg peak of the charged particle beam $B_4$ of Comparative Example 1. For this reason, the charged particle beam irradiation apparatus 1 of the present embodiment can further reduce the number of energies of the charged particle beam B having a Bragg peak required to form the same spread out Bragg peak than the charged particle beam irradiation apparatus 100 of Comparative Example 1. Accordingly, the controller 80 of the charged particle beam irradiation apparatus 1 further reduces the number of times of switching the energy of the charged particle beam B than a controller of the charged particle beam irradiation apparatus 100 of Comparative Example 1. The charged particle beam irradiation apparatus 1 can further shorten the time of irradiation of the charged particle beam B than the charged particle beam irradiation apparatus 100 of Comparative Example 1.

Here, in the charged particle beam irradiation apparatus 100 of Comparative Example 1, a case where the charged particle beam after passing through the energy degrader 153 is a charged particle beam of the same energy as that of the charged particle beam $B_2$ in the charged particle beam irradiation apparatus 1 of the present embodiment, instead of the charged particle beam $B_3$, can be considered. The charged particle beam irradiation apparatus is a charged particle beam irradiation apparatus of Comparative Example 2, and the water equivalent thickness of the snout degrader is appropriately changed. In this case, the charged particle beam $B_2$ after passing through the energy degrader of Comparative Example 2 becomes a charged particle beam $B_5$, of which the energy distribution is limited to the range of the region $E_1$ by the momentum resolving aperture. For this reason, the charged particle beam $B_2$ in the irradiator 3 of the charged particle beam irradiation apparatus 1 of the present embodiment has a larger spread of momentum than that of the charged particle beam $B_5$ in an irradiator. The Bragg peak of the charged particle beam $B_2$ in the charged particle beam irradiation apparatus 1 of the present embodiment is thicker than the Bragg peak of the charged particle beam $B_5$ in the charged particle beam irradiation apparatus of Comparative Example 2. For this reason, the charged particle beam irradiation apparatus 1 of the present embodiment which is not provided with the momentum resolving aperture 157 can further shorten the time of irradiation of the charged particle beam B than the charged particle beam irradiation apparatus of Comparative Example 2.

As described above, the transporter 4 of the charged particle beam irradiation apparatus 1 of the present embodiment can transport the charged particle beam $B_2$ from the energy degrader 43 to the irradiator 3 without being provided with the momentum resolving aperture that selects an energy in a specific range among the energies of the charged particle beam $B_2$. Particularly, therefore, the charged particle beam $B_2$ of the present embodiment has a thicker Bragg peak than those of the charged particle beams $B_4$ and $B_5$ in a case where the momentum resolving aperture is provided (Comparative Example 1 and Comparative Example 2). Therefore, in the charged particle beam irradiation apparatus 1, the number of energies of the charged particle beam B required to form a spread out Bragg peak is reduced, and the number of times of switching the energy of the charged particle beam B is reduced. As described above, the charged particle beam irradiation apparatus 1 can shorten the time of irradiation of the charged particle beam B.

In addition, in the charged particle beam irradiation apparatus 1 according to the present embodiment, the momentum resolving aperture is not provided inside the gantry 5 as in the related art. When the momentum resolving aperture is accommodated in the gantry, since an unnecessary neutron ray is generated from a proton beam that stops at the momentum resolving aperture, it is considered that the unnecessary neutron ray to the patient is increased. However, since the charged particle beam irradiation apparatus 1 of the present embodiment does not include the momentum resolving aperture, the generation of an unnecessary neutron ray can be suppressed.

In addition, in the charged particle beam irradiation apparatus 1 according to the present embodiment, the collimator 44 can adjust the shape, size, and divergence of the charged particle beam B that has passed through the energy degrader 43, and the charged particle beam B can be transported from the energy degrader 43 to the irradiator 3 while the energy distribution of the charged particle beam B is maintained. At this time, since the shape, size, and divergence of the charged particle beam B are adjusted by the collimator 44, for example, the charged particle beam B can pass through the inside of the duct 11 without coming into contact with the duct 11 of the irradiator 3 downstream of the collimator 44.

In addition, in the charged particle beam irradiation apparatus 1 according to the present embodiment, since the transporter 4 has a hole diameter that allows the charged particle beam $B_2$ to pass therethrough, the transporter 4 can transport the charged particle beam $B_2$ from the energy degrader 43 to the irradiator 3 while maintaining the energy distribution of the charged particle beam $B_2$ without selecting an energy in a specific range for the charged particle beam $B_2$.

The snout degrader 30 of the charged particle beam irradiation apparatus 1 of the present embodiment has a larger water equivalent thickness than that of the snout degrader of the charged particle beam irradiation apparatus 100 of Comparative Example 1. The reason is that since the charged particle beam $B_2$ has a larger energy than that of the charged particle beam $B_4$, the tumor 14 (irradiation target) located in a shallow site of the patient 15 can be irradiated therewith.

Since the energy degrader 43 of the charged particle beam irradiation apparatus 1 of the present embodiment causes the momentum dispersion of the charged particle beam $B_2$ to be less than 6%, the spread of the energy distribution of the charged particle beam $B_2$ can be further suppressed than that of the charged particle beam $B_3$. Here, in the charged particle beam irradiation apparatus 1 of the present embodiment, a case where the charged particle beam of the irradiator 3 is a charged particle beam of the same energy as that of the charged particle beam $B_3$ on the upstream side of the momentum resolving aperture 157 in the charged particle beam irradiation apparatus 100 of Comparative Example 1, instead of the charged particle beam $B_2$, is considered. The charged particle beam irradiation apparatus is a charged particle beam irradiation apparatus of a modification example (another embodiment of the present invention), and the water equivalent thickness of the snout degrader is appropriately changed. As described above, the momentum dispersion of the charged particle beam $B_3$ is 6% or more. In this case, the charged particle beam $B_3$ having a larger spread of momentum than that of the charged particle beam $B_2$, namely, the charged particle beam $B_3$ having a larger beam diameter than that of the charged particle beam $B_2$ passes through the transporter. Therefore, when the charged particle beam $B_3$ is adopted, the hole diameter of the transporter needs to be larger than that in the case of the charged particle beam $B_2$. In addition, when the charged particle beam $B_3$ having a larger beam diameter than that of the charged particle beam $B_2$ comes into contact with the bending electromagnet downstream of the transporter or the duct of the irradiator to dissipate, there is a possibility that the charged particle beam irradiation apparatus of the modification example is radioactivated, or there is a possibility that the unnecessary radiation dose is increased. In order to suppress the possibility, when the charged particle beam $B_3$ is adopted, the duct, the bending electromagnet, and the like of the charged particle beam irradiation apparatus of the modification example need to be further increased in size than those in the case of the charged particle beam $B_2$.

As described above, since the charged particle beam irradiation apparatus 1 of the present embodiment transforms the charged particle beam B on the downstream side of the energy degrader 43 into the charged particle beam $B_2$ having a momentum dispersion of less than 6%, the charged particle beam irradiation apparatus 1 can further suppress a large increase in size of the facility, and can properly further reduce the footprint than the charged particle beam irradiation apparatus of the modification example. In addition, the charged particle beam irradiation apparatus 1 of the present embodiment can further suppress radioactivation of the facility and the unnecessary radiation dose while suppressing a large increase in size of the facility than the charged particle beam irradiation apparatus of the modification example.

Incidentally, in the charged particle beam irradiation apparatus of the modification example, since the energy selection system 150 does not need to be provided in the transporter, the shape of the transporter 4 can be more freely changed according to an environment in which the transporter 4 is disposed than in the charged particle beam irradiation apparatus 100 of Comparative Example 1. For example, even in the charged particle beam irradiation apparatus of the modification example, the transporter 4 can be made linear. Accordingly, the charged particle beam irradiation apparatus of the modification example can properly further reduce the footprint than the charged particle beam irradiation apparatus 100 of Comparative Example 1. In addition, the Bragg peak of the charged particle beam $B_3$ in the irradiator of the charged particle beam irradiation apparatus of the modification example is thicker than the Bragg peak of the charged particle beam $B_4$ in the irradiator of Comparative Example 1. Accordingly, the charged particle beam irradiation apparatus of the modification example can further shorten the time of irradiation of the charged particle beam B than the charged particle beam irradiation apparatus 100 of Comparative Example 1.

Here, as an example, the range of the charged particle beam B (proton beam) of each energy will be summarized. The range of the charged particle beam B of 60 MeV is 3 cm, the range of the charged particle beam B of 70 MeV is 4 cm, and the range of the charged particle beam B of 110 MeV is 9 cm. When the charged particle beam B is exited toward water, the beam diameter of the charged particle beam B (proton beam) of each energy at a water depth of 4 cm is provided as an example. The charged particle beam B of 60 MeV does not reach a water depth of 4 cm. The beam diameter of the charged particle beam B of 70 MeV at a water depth of 4 cm is 10 mm. When the water equivalent thickness of the snout degrader 30 is set to 5 cm, the beam diameter of the charged particle beam B of 110 MeV at a water depth of 4 cm is 7 mm.

Subsequently, when the charged particle beam B is exited toward water, the beam diameter of the charged particle beam B (proton beam) of each energy at a water depth of 2 cm is provided as an example. When the water equivalent thickness of the snout degrader is set to 1 cm, the beam diameter of the charged particle beam B of 60 MeV at a water depth of 2 cm is 11 mm. When the water equivalent thickness of the snout degrader is set to 2 cm, the beam diameter of the charged particle beam B of 70 MeV at a water depth of 2 cm is 10 mm. When the water equivalent thickness of the snout degrader 30 is set to 7 cm, the beam diameter of the charged particle beam B of 110 MeV at a water depth of 2 cm is 7 mm. The water depths for the charged particle beam B can be unified by changing the thickness of the snout degrader 30 for each magnitude of the energy of the charged particle beam B.

From the above results, in the charged particle beams B having a plurality of different energies, the beam sizes at the same water depth are the smallest when the water equivalent thickness of the snout degrader 30 for the charged particle beam B of 110 MeV is appropriately set. Accordingly, when an exit target of the charged particle beam $B_2$ is located in a shallow region, the charged particle beam $B_2$ having an energy of 80 MeV to 150 MeV when exited under conditions of a combination of the snout degrader 30 has a smaller beam diameter than that of the charged particle beam B of a lower energy (for example, 70 MeV) than that of the charged particle beam $B_2$. For this reason, when the tumor 14 (irradiation target) of the patient 15 is located in a shallow region, the charged particle beam irradiation apparatus 1 can perform the irradiation of the charged particle beam $B_2$ of, for example, 80 MeV to 150 MeV according to the position, size or shape of the tumor 14. Incidentally, when the tumor 14 (irradiation target) is located in a shallow region, for example, the charged particle beam irradiation apparatus 1 may perform the irradiation of the charged particle beam $B_2$ of 90 MeV to 150 MeV, may perform the irradiation of the charged particle beam $B_2$ of 100 MeV to 150 MeV, or may perform the irradiation of the charged particle beam $B_2$ of 110 MeV to 150 MeV. In addition, when the tumor 14 (irradiation target) is located in a deep region, or the like, the charged particle beam irradiation apparatus 1 may perform the irradiation of the charged particle beam $B_2$ of, for example, 150 MeV or more.

In addition, the ratio of the lowering of the energy from the charged particle beam $B_1$ to the charged particle beam $B_2$ in the transporter 4 of the present embodiment is smaller than that when the energy is lowered from the charged particle beam $B_1$ to the charged particle beam $B_3$ in the transporter of the modification example. For this reason, in the present embodiment, the energy transport efficiency in the process of transport of the charged particle beam B in the transporter 4 from the accelerator 2 to the irradiator 3 is higher than the energy transport efficiency of the modification example. In the present embodiment, the beam current at the isocenter AC in the gantry 5 is further raised than the beam current at the isocenter of the modification example, and the time of irradiation for the tumor 14 (irradiation target) of the patient 15 can be shortened.

Since the selection of an energy is not performed for the charged particle beam $B_2$ of the charged particle beam irradiation apparatus 1 of the present embodiment in the momentum resolving aperture 157 as for the charged particle beam $B_4$ of Comparative Example 1 and the charged particle beam $B_5$ of Comparative Example 2, there is a possibility that the symmetry of the cross-sectional shape of the beam inside the irradiator 3 cannot be secured. However, when the charged particle beam $B_2$ passes through the duct 11 of the irradiator 3, the charged particle beam $B_2$ is scattered by the atmosphere (air) inside the duct 11. Accordingly, even when the charged particle beam irradiation apparatus 1 does not include the momentum resolving aperture (energy selection system), the symmetry of the cross-sectional beam shape of the charged particle beam $B_2$ is secured. Therefore, the irradiator 3 can irradiate a proper range with the charged particle beam $B_2$.

The internal path 4B of the transporter 4 includes the bending magnet (bending electromagnet 8) that has hexapole components and causes the charged particle beam $B_2$ to converge to trim the shape of the charged particle beam $B_2$. For this reason, the internal path 4B of the transporter 4 can trim the shape of the charged particle beam $B_2$ according to the energy distribution of the charged particle beam $B_2$ passing therethrough, and can properly transport the charged particle beam $B_2$ from the accelerator 2 to the irradiator 3.

The present invention is not limited to the above-described embodiments.

For example, the energy degrader 43 may reduce the energy of the charged particle beam B, which is generated by the accelerator, such that the momentum dispersion of the charged particle beam B is 6% or more. In this case, each portion of the transporter 4 has a hole diameter that allows the charged particle beam B to pass therethrough. The collimator 44 may not be provided between the energy degrader 43 and the irradiator 3. In this case, each portion of the transporter 4 has a hole diameter that allows the charged particle beam B to pass therethrough. The inside of the duct 11 may be in a vacuum state, or the inside of the duct 11 may be filled with rare gas. The rare gas is, for example, argon gas. The bending electromagnet 8 located in the internal path 4B of the transporter 4 may not be a hexapole magnet or a bending magnet including hexapole components.

In addition, the structure of the building 6 or the layout of each of the components may be appropriately changed without departing from the concept of the present invention.

It should be understood that the invention is not limited to the above-described embodiment, but may be modified into various forms on the basis of the spirit of the invention. Additionally, the modifications are included in the scope of the invention.

What is claimed is:

1. A charged particle beam irradiation apparatus that performs irradiation of a charged particle beam, the apparatus comprising:
   an accelerator that accelerates a charged particle to generate the charged particle beam;
   an irradiator that performs irradiation of the charged particle beam generated by the accelerator; and
   a transporter that includes a degrader provided outside the irradiator to reduce an energy of the charged particle beam generated by the accelerator, and transports the charged particle beam, which is generated by the accelerator, to the irradiator,
   wherein the transporter transports the charged particle beam to the irradiator while maintaining an energy distribution of the charged particle beam that is reduced in energy by the degrader, and
   a hole diameter of the transporter on a downstream side of the degrader is larger than a hole diameter of the transporter on an upstream side of the degrader.

2. The charged particle beam irradiation apparatus according to claim 1,
   wherein the accelerator includes a vacuum chamber that accelerates the charged particle while causing the charged particle to orbit on an acceleration plane inside the vacuum chamber, a charged particle source that supplies the charged particle into the vacuum chamber, and a deflector.

3. The charged particle beam irradiation apparatus according to claim 2,
   wherein the vacuum chamber is connected to an external path of the transporter, and
   the deflector extracts the charged particle orbiting inside the vacuum chamber to supply the charged particle to the external path of the transporter.

4. The charged particle beam irradiation apparatus according to claim 1,
   wherein the transporter includes a collimator that is provided between the degrader and the irradiator to adjust a shape, a size, and divergence of the charged particle beam.

5. The charged particle beam irradiation apparatus according to claim 1,
   wherein the transporter further includes a quadrupole electromagnet, a steering electromagnet, and a beam stopper.

6. The charged particle beam irradiation apparatus according to claim 1,
   wherein the transporter has a hole diameter that allows the charged particle beam, which is reduced in energy by the degrader, to pass through the transporter.

7. The charged particle beam irradiation apparatus according to claim 1,
   wherein the degrader reduces the energy of the charged particle beam, which is generated by the accelerator, such that a momentum dispersion of the charged particle beam is less than 6%.

8. The charged particle beam irradiation apparatus according to claim 1,
   wherein the irradiator further includes a scanning electromagnet that scans the charged particle beam, a duct through which the charged particle beam scanned by the scanning electromagnet passes, and a monitor that detects the charged particle beam which has passed through the duct, and
   an inside of the duct is exposed to an atmosphere.

9. The charged particle beam irradiation apparatus according to claim 8,
   wherein the scanning electromagnet includes a first direction scanning electromagnet that scans the charged particle beam in a first direction, and a second direction scanning electromagnet that scans the charged particle beam in a second direction intersecting the first direction, and
   the first direction scanning electromagnet and the second direction scanning electromagnet each are formed of a pair of electromagnets.

10. The charged particle beam irradiation apparatus according to claim 8,
    wherein the duct is disposed downstream of the scanning electromagnet to guide the charged particle beam, which is scanned by the scanning electromagnet, to the monitor disposed downstream of the duct.

11. The charged particle beam irradiation apparatus according to claim 10,
wherein the duct has a truncated cone shape that is widened as extending from the scanning electromagnet toward the monitor, and is penetrated along a base axis.

12. The charged particle beam irradiation apparatus according to claim 10,
wherein the duct is disposed on the base axis, and
the base axis is a reference line that serves as a reference when the irradiator performs the irradiation of the charged particle beam, and the base axis is perpendicular to a center line of the rotary unit, and passes through the center line to pass through an isocenter on the center line of the rotary unit.

13. The charged particle beam irradiation apparatus according to claim 1,
wherein the irradiator further includes a collimator that blocks a part of the charged particle beam and allows a part of the charged particle beam to pass through the collimator, and
a snout degrader that reduces the energy of the charged particle beam, which passes through the snout degrader, to shift a range of the charged particle beam.

14. The charged particle beam irradiation apparatus according to claim 13, further comprising:
an irradiation nozzle that accommodates the snout degrader,
wherein the snout degrader is provided in a tip part of the irradiation nozzle, and
a water equivalent thickness of the snout degrader is approximately 10 cm.

15. The charged particle beam irradiation apparatus according to claim 1,
wherein the transporter includes a hexapole magnet or a bending magnet including hexapole components, which causes the charged particle beam to converge to trim a shape of the charged particle beam.

16. The charged particle beam irradiation apparatus according to claim 15,
wherein the bending magnet includes the hexapole components, each of which has a convex shape or a concave shape, in the transporter, and a trajectory which differs depending on momentum is corrected by the bending magnet.

17. The charged particle beam irradiation apparatus according to claim 15,
wherein the hexapole components of the bending magnet include auxiliary coils, and
a trajectory which differs depending on momentum is corrected by the bending magnet.

18. The charged particle beam irradiation apparatus according to claim 1,
wherein the irradiator includes a rotary unit rotatable around a rotation axis, and
the transporter extends linearly from the accelerator toward the rotary unit.

19. The charged particle beam irradiation apparatus according to claim 1,
wherein the transporter does not have a member which adjusts the energy distribution between the degrader and the irradiator.

* * * * *